(12) United States Patent
Dillard et al.

(10) Patent No.: US 6,214,876 B1
(45) Date of Patent: Apr. 10, 2001

(54) INDENE-1-ACETAMIDE $sPLA_2$ INHIBITORS

(75) Inventors: Robert D. Dillard, Zionsville, IN (US); Sanji Hagishita, Gose; Mitsuaki Ohtani, Nara, both of (JP)

(73) Assignees: Eli Lilly and Company, Indianapolis, IN (US); Shionogi & Company, Ltd., Osaka (JP)

( * ) Notice: Subject to any disclaimer, the term of this patent is extended or adjusted under 35 U.S.C. 154(b) by 0 days.

(21) Appl. No.: 08/278,441

(22) Filed: Jul. 21, 1994

(51) Int. Cl.$^7$ ............... A61K 31/195; C07C 233/03
(52) U.S. Cl. ............... 514/563; 514/561; 562/428; 562/441
(58) Field of Search ............... 514/569, 561, 514/563; 562/427, 437, 466, 428, 441

(56) References Cited

U.S. PATENT DOCUMENTS

| | | | |
|---|---|---|---|
| 2,825,734 | 3/1958 | Speeter | 260/319 |
| 3,196,162 | 7/1965 | Sarett | 260/319 |
| 3,242,163 | 3/1966 | Sarett et al. | 260/211 |
| 3,242,193 | 3/1966 | Sarrett | 260/319 |
| 3,259,622 | 7/1966 | Shen et al. | 260/247.5 |
| 3,449,363 | 6/1969 | Littell | 260/326.13 |
| 3,624,103 | 11/1971 | DeMartilis et al. | 260/326.13 A |
| 3,888,902 * | 6/1975 | Shen et al. | 562/466 |
| 3,954,852 * | 5/1976 | Shen et al. | 562/466 |
| 4,012,451 | 3/1977 | Birchall et al. | 424/251 |
| 5,093,356 * | 3/1992 | Girard et al. | 562/623 |
| 5,132,319 | 7/1992 | Girard | 514/415 |
| 5,286,889 * | 2/1994 | Lipushutz et al. | 556/28 |
| 5,403,188 * | 4/1995 | Oxman et al. | 433/218 |
| 5,405,957 * | 4/1995 | Tang et al. | 540/472 |
| 5,405,981 * | 4/1995 | Lipshutz | 556/112 |

FOREIGN PATENT DOCUMENTS

| | | |
|---|---|---|
| 0519353 | 12/1992 | (EP) . |
| 620214A | 10/1994 | (EP) . |
| 620215A | 10/1994 | (EP) . |
| WO88/06885 | 9/1988 | (WO) . |

OTHER PUBLICATIONS

Andreani, A. et al., "Nonsteroidal Antiinflammatory Agents. 2. Synthesis and Biological Activity of 2—Chlorindolecarboxylic Acids"; *Journal of Medicinal Chemistry*, vol. 20, No. 10, 1977, pp. 1344–1346.

Julia, Marc, et al., "No. 208—Recherches en serie indolique. XIII. Sur quelques methoxy—5 et. —6 tryptamines", *Bulletin de La Societe Chimique de France*, Paris, France; 1965, pp. 1411–1417.

Chemical Abstracts, vol. 1/2. No. 24, Abstract No. 223181s; "Kinetis of hydrolysis of indomethacin and indomethacin ester predrigs in aqueous solution" Jun. 11, 1990, p. 407.

Chemical Abstracts Service, "Registry Handbook", Number Section, Registry Numbers (see, CAS RN 6264–33–1) 1965–1971, Publ. American Chemical Society.

Von K. H. Boltze; O. Brendler, et.al., "Chemische Struktur und antiphlogistische Wirkung in der Reihe der substituierten Indol–3–essigsauren", *Arznermittel Forschung Drug Research*, vol. 30 (II), No. 8A, 1980, Aulendorf, DE, pp. 1314–1325.

Kramer, Ruther et al., "Structure and Properties of a Human Non–Pancreatic Phospholipase $A_2$", *The Journal of Biological Chemistry*, 264.10, Apr. 5, 1989, pp. 5768–5775.

Seilhamer, Jeffery, et al., "Cloning and Recombinant Expression of Phospholipase $A_2$ present in Pheumatoid Arthritic Synovial Fluid"; *The Journal of Biological Chemistry*, 254:10, Apr. 5, 1989, pp. 5335–5338.

Kreft, A; Nelson, J. et al, "Structure–activity relationships leading to WAY–121,520, a tris aryl type. Nidomethacin–based phospholipase A2 (PLA2)/leukotriene biosynthesis inhibitor", Issue vol. 39 (1993), pp. C33–C35, ISSN 0065–4299; publ. by Birkhauser Verlag, Basel Switzerland; (Proceedings of the Sixth International Research Assoc., Sep. 20–24, 1992 at White Haven, PA/USA, Ed., D.W. Morgan and A.K. Welton.

Cingolani, GM, et al., "Idolizine derivatives with biological activity VI 1–(2–aminoethyl)–3–benzl–7–methoxy–2–methylindolizine, benanser in structural analogue", *Eur. J. Med. Chem.* (1990) 25, pp. 709–712.

\* cited by examiner

Primary Examiner—Richard L. Raymond
(74) *Attorney, Agent, or Firm*—Roger S. Benjamin

(57) ABSTRACT

Indene-1-acetamide compounds of the general formula (I) below;

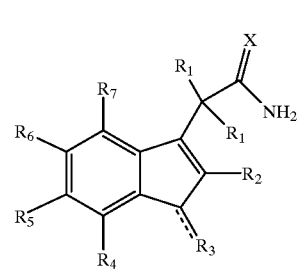

(I)

inhibit $sPLA_2$ mediated release of fatty acids and are useful for treatment of conditions such as septic shock.

12 Claims, No Drawings

INDENE-1-ACETAMIDE SPLA₂ INHIBITORS

FIELD OF THE INVENTION

This invention relates to novel indene compounds useful for inhibiting sPLA$_2$ mediated release of fatty acids for conditions such as septic shock.

BACKGROUND OF THE INVENTION

The structure and physical properties of human non-pancreatic secretory phospholipase A$_2$ (hereinafter called, "sPLA$_2$") has been thoroughly described in two articles, namely, "Cloning and Recombinant Expression of Phospholipase A$_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase A$_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

It is believed that sPLA$_2$ is a rate limiting enzyme in the arachidonic acid cascade which hydrolyzes membrane phospholipids. Thus, it is important to develop compounds which inhibit sPLA$_2$ mediated release of fatty acids (e.g., arachidonic acid). Such compounds would be of value in general treatment of conditions induced and/or maintained by overproduction of sPLA$_2$; such as septic shock, adult respiratory distress syndrome, pancreatitis, trauma, bronchial asthma, allergic rhinitis, rheumatoid arthritis, and etc.

U.S. Pat. No. 2,825,734 describes the preparation of 3-(2-amino-1-hydroxyethyl) indoles using 3-indole glyoxylamide intermediates such as 1-phenethyl-2-ethyl-6-carboxy-N-propyl-3-indoleglyoxylamide (see, Example 30).

U.S. Pat. No. 2,890,233 describes several amide derivatives of 3-indoleacetic acids.

U.S. Pat. Nos. 3,196,162; 3,242,162; 3,242,163; and 3,242,193 (see, Col. 3, lines 55–60, Example 56) describe indolyl aliphatic acids together with their related esters and amides.

U.S. Pat. No. 3,449,363 describes trifluoromethylindoles having glyoxylamide groups at the 3 position of the indole nucleus. These compounds are stated to be analgesics.

U.S. Pat. No. 5,132,319 describes certain 1-(hydroxylaminoalkyl)indoles derivatives as inhibitors of leukotriene biosynthesis.

The article, "Structure-activity relationships leading to WAY-121,520, a tris aryl-type, indomethacin-based, phospholipase A$_2$ (PLA$_2$)/leukotriene biosynthesis inhibitor", by A Kreft, et. al., *Agents and Actions, Special Conference Issue* Vol. 39 (1993), pp. C33–C35, ISSN 0065–4299, published by Birkhauser Verlag, Basel Switzerland; (Proceedings of the Sixth International Conference of the Inflammation Research Association, Sep. 20–24, 1992, at White Haven, PA/USA, Guest Editors, D. W. Morgan and A. K. Welton) describes the inhibition of phospholipase A2 by indomethacin analogs. Indole compounds having benzyl and acidic substituents are described.

The article, (Short communication) entitled, "Indolizine derivatives with biological activity VI 1-(2-aminoethyl)-3-benzyl-7-methoxy-2-methylindolizine, benanserin structural analogue" by G M Cingolani, F. Claudi, M. Massi, and F. Venturi, *Eur. J. Med. Chem.* (1990) 25, pp. 709–712 published by Elsevier, Paris describes selected indolizines and their activity on smooth muscle.

European Patent Application No. 0 519 353 (Application No. 92109968.5) describes indolizin derivatives which have pharmacological activities such as inhibitory activity on testosteron reductase.

It is desirable to develop new compounds and treatments for sPLA$_2$ induced diseases.

SUMMARY OF THE INVENTION

This invention is a novel use of indene compounds having the nucleus and substituent numbering shown below:

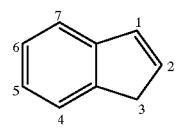

Moreover, the indene compounds of the invention have the general configurations shown in structural formulae "G" below:

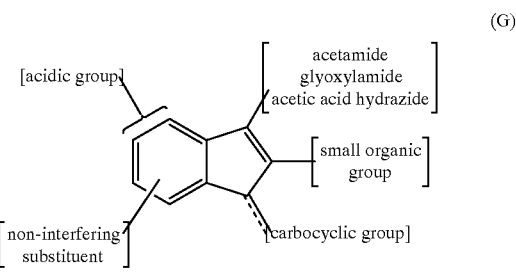

(G)

In formula "G" an acetamide, acetic acid hydrazide, or glyoxylamide moiety is present at the 1 position; a large (C$_7$-C$_{30}$) organic (e.g., carbocyclic) group is present at the 3 position and is attached to the indene nucleus with a single, or optionally, a double bond; an acidic group is substituted at the 6 or 7 position, and a small organic group is substituted at the 2 position.

This invention is also a pharmaceutical composition containing indene-1-functional compounds represented by the general formulae "G" and mixtures thereof.

This invention is also a method of preventing and treating septic shock, adult respiratory distress syndrome, pancreatitis, trauma, bronchial asthma, allergic rhinitis, rheumatoid arthritis, and related diseases by contact with a therapeutically effective amount of indene-1-functional compounds selected from the group consisting of the novel indene compounds represented by the general formulae "G".

DETAILED DESCRIPTION OF THE INVENTION

Definitions

The indene acetamides, acetic acid hydrazides (hereinafter called, "hydrazides), and glyoxylamides of the invention employ certain terms defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, n-pentyl, and n-hexyl.

The term, "alkenyl" employed alone or in combination with other terms means a straight chain or branched monovalent hydrocarbon group having the stated number range of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chloro, bromo, or iodo.

The term, "heterocyclic radical", refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridinyl, phenylpyridinyl, benzylpyridinyl, pyrimidinyl, phenylpyrimidinyl, pyrazinyl, 1,3,5-triazinyl, quinolinyl, phthalazinyl, quinazolinyl, and quinoxalinyl.

The term, "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are benzylidene, cycloalkyl, cycloalkenyl, phenyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

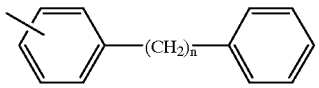

(bb)

where n is a number from 1 to 8.

The term, "non-interfering substituent", refers to radicals suitable for substitution at positions 4, 5, 6, and/or 7 on the indene nucleus (as hereinafter depicted in Formula I) and radical(s) suitable for substitution on the heterocyclic radical and carbocyclic radical as defined above. Illustrative non-interfering radicals are $C_1$–$C_6$ alkyl, $C_1$–$C_6$ alkenyl, $C_1$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —$(CH_2)_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —$(CH_2)_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl; where n is from 1 to 8.

The term, "acidic group" means an organic group which when attached to an indene nucleus, through suitable linking atoms (hereinafter defined as the "acid linker"), acts as a proton donor capable of hydrogen bonding. Illustrative of an acidic group are the following:

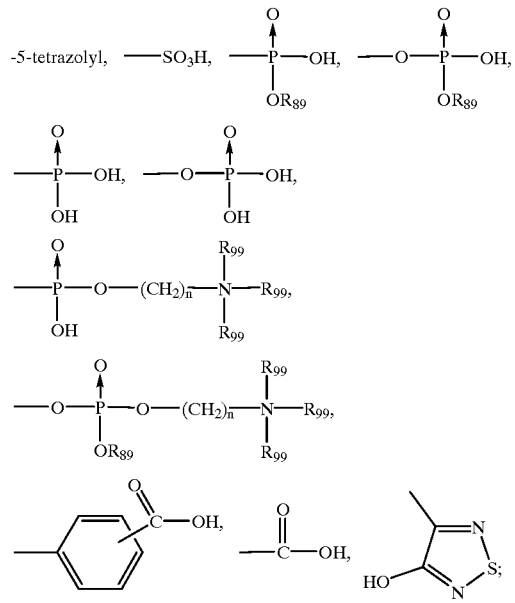

where n is 1 to 8, $R_{89}$ is a metal or $C_1$–$C_{10}$ alkyl, and $R_{99}$ is hydrogen or $C_1$–$C_{10}$ alkyl.

The words, "acid linker" refer to a divalent linking group symbolized as, —($L_a$)—, which has the function of joining the indene nucleus to an acidic group in the general relationship:

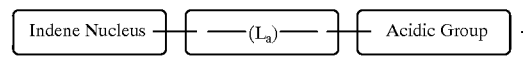

The words, "acid linker length", refer to the number of atoms (excluding hydrogen) in the shortest chain of the linking group —($L_a$)— that connects the indene nucleus with the acidic group. The presence of a carbocyclic ring in —($L_a$)— counts as the number of atoms approximately equivalent to the calculated diameter of the carbocyclic ring. Thus, a benzene or cyclohexane ring in the acid linker counts as 2 atoms in calculating the length of —($L_a$)—. Illustrative acid linker groups are;

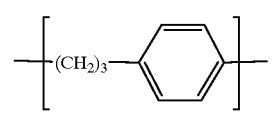

(a)

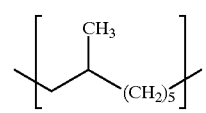

(b)

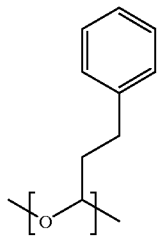

wherein, groups (a), (b), and (c) have acid linker lengths of 5, 7, and 2, respectively.

The term, "amine", includes primary, secondary and tertiary amines.

The Indene Compounds of the Invention:

There are three types of Indene compounds of the invention as represented by structural formulae (I), (II), and (III) below:

1) The indene-3-acetamides are represented by the formula (I), below

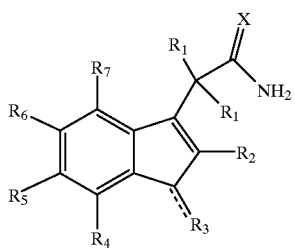

where X is oxygen or sulfur and each $R_1$ is independently hydrogen, $C_1$–$C_3$ alkyl, or halo and all other groups are as hereinafter defined.

2) The indene-1-hydrazides are represented by the formula (II), as set out below:

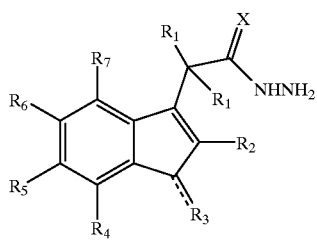

where X is oxygen or sulfur and each $R_1$ is independently hydrogen, $C_1$–$C_3$ alkyl, or halo and all other groups are as hereinafter defined.

3) The indene-3-glyoxylamides are represented by the formula (III), as set out below:

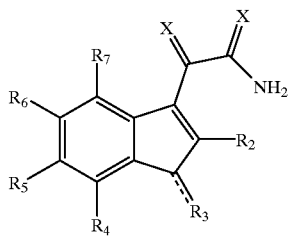

where X is independently oxygen or sulfur and all other groups are as hereinafter defined.

For formulae (I), (II), and (III) above the remaining groups are defined as follows:

$R_3$ is selected from groups (a), (b) and (c) where;
(a) is $C_7$–$C_{20}$ alkyl, $C_7$–$C_{20}$ alkenyl, $C_7$–$C_{20}$ alkynyl, carbocyclic radical, or heterocyclic radical, or
(b) is a member of (a) substituted with one or more independently selected non-interfering substituents; or
(c) is the group —(L)—$R_{80}$; where, —(L)— is a divalent linking group of 1 to 12 atoms and where $R_{80}$ is a group selected from (a) or (b);

$R_2$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen; (that is, the $R_{12}$ radical may contain hydrogen atoms, but the remaining atoms comprising the total of 1 to 3 are non-hydrogen);

$R_6$ and $R_7$ are independently selected from hydrogen, a non-interfering substituent, or the group, —($L_a$)— (acidic group); wherein —($L_a$)—, is an acid linker having an acid linker length of 1 to 10; provided, that at least one of $R_6$ and $R_7$ must be the combined group, —($L_a$)— (acidic group); and $R_4$ and $R_5$ are each independently selected from hydrogen, non-interfering substituent, carbocyclic radical, carbocyclic radical substituted with non-interfering substituents, heterocyclic radical, and heterocyclic radical substituted with non-interfering substituents.

Preferred Subgroups of Indene Compounds of the Invention:

A preferred subclass of compounds of formulae (I), (II), and (III) are those wherein all x are oxygen.

Another preferred subclass of compounds of formulae (I), (II), and (III) are those wherein $R_2$ is selected from the group; halo, cyclopropyl, methyl, ethyl, —O—methyl, and —S—methyl.

Another preferred subclass of compounds of formulae (I), (II) and (III) are those wherein for $R_3$, —(L)— is selected from the group consisting of:

—C≡C—,
—CH=CH=13 ,
—CH$_2$—,
—(CH$_2$)$_2$—, —(CH$_2$)$_s$—S—, —(CH$_2$)$_s$—O—, and

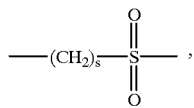

where s is 0 or 1.

Another preferred subclass of compounds of formulae (I), (II), and (III) are those wherein for $R_3$, group $R_{80}$ is carbocyclic, attached to the indene ring with a double or single bond, and is selected from the group consisting of benzylidene, cycloalkyl, cycloalkenyl, phenyl, naphthyl, norbornanyl, bicycloheptadienyl, toluyl, xylenyl, indenyl, stilbenyl, terphenylyl, diphenylethylenyl, phenylcyclohexenyl, acenaphthylenyl, and anthracenyl, biphenyl, bibenzylyl and related bibenzylyl homologues represented by the formula (bb),

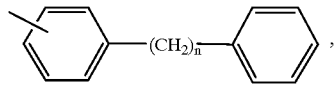
(bb)

where n is a number from 1 to 8. Particularly preferred are compounds wherein $R_3$ is selected from the group consisting of

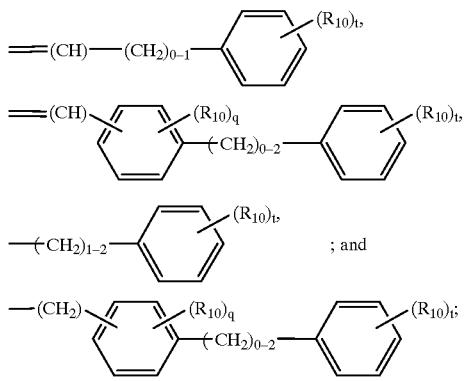

where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl, q is a number from 0 to 4, and t is a number from 0 to 5.

Another preferred subclass of compounds of formulae (I), (II), and (III) are those wherein $R_7$ comprises an acidic group and the acid linker for the $R_7$ acidic group has an acid linker length of 2 or 3 and the acid linker group, —($L_a$)—, for $R_7$ is selected from the group represented by the formula;

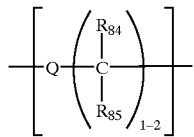

where Q is selected from the group —(CH$_2$)—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo. Most preferred are compounds where the acid linker, —($L_a$)—, for $R_7$ is selected from the specific groups;

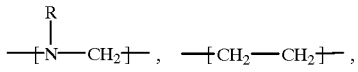

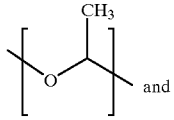

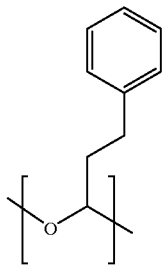

where R is H or $C_1$–$C_4$ alkyl.

Another preferred subclass of compounds of formulae (I), (II), and (III) are those wherein $R_6$ comprises an acidic group and the acid linker of the $R_6$ acidic group has an acid linker with an acid linker length of 3 to 10 atoms and the acid linker group, —($L_a$)—, for $R_6$ is selected from;

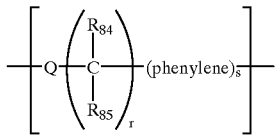

where r is a number from 1 to 7, s is 0 or 1, and Q is selected from the group —(CH$_2$)—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo. Most preferred are compounds where the acid linker, —($L_a$)—, for $R_6$ is selected from the specific groups;

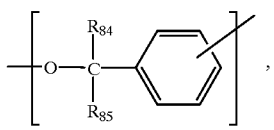

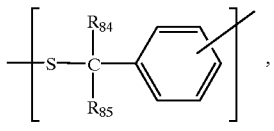

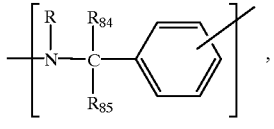

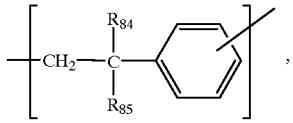

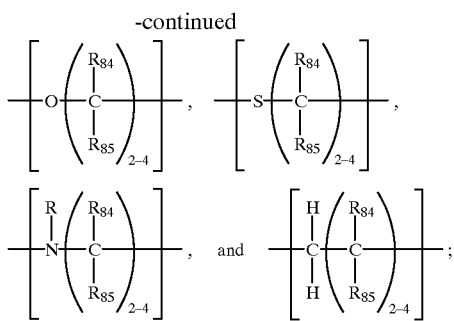

wherein; R is hydrogen or $C_1$–$C_4$ alkyl, $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo.

Another preferred subclass of compounds of formulae (I), (II), (III) are those wherein the acidic group (or salt, and prodrug derivatives thereof) on $R_6$ and/or $R_7$ is selected from the following:

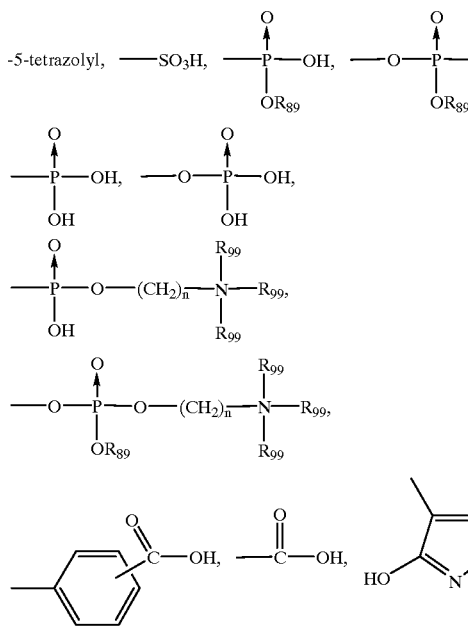

where n is 1 to 8, $R_{89}$ is a metal or $C_1$–$C_{10}$ alkyl, and $R_{99}$ is hydrogen or $C_1$–$C_{10}$ alkyl. Particularly preferred are compounds wherein the acidic group of $R_6$ and $R_7$ is selected from;

—$CO_2H$,
—$SO_3H$,
—$P(O)(OH)_2$, or salt, and prodrug (e.g., ester) derivatives thereof. The carboxyl group is the most preferred acidic group. It is highly preferred that only one of $R_6$ or $R_7$ contain an acidic group.

Another preferred subclass of compounds of formula (I), (II), and (III) are those wherein $R_4$ and $R_5$ are each independently selected from hydrogen and non-interfering substituents, with the non-interfering substituents being selected from the group consisting of $C_1$–$C_6$ alkyl, $C_1$–$C_6$ alkenyl, $C_1$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —($CH_2$)$_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —($CH_2$)$_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$–$C_6$ carbonyl; where n is from 1 to 8.

Specific preferred compounds of the invention are represented by formulae 14a, and 14b and acceptable salts, solvates and prodrug derivatives thereof:

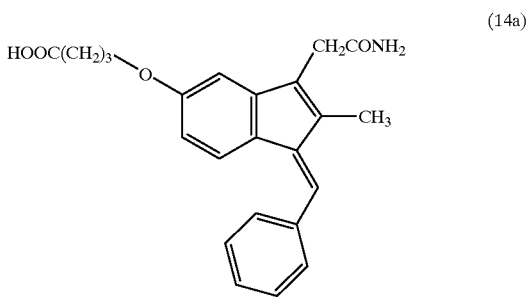

(14a)

and

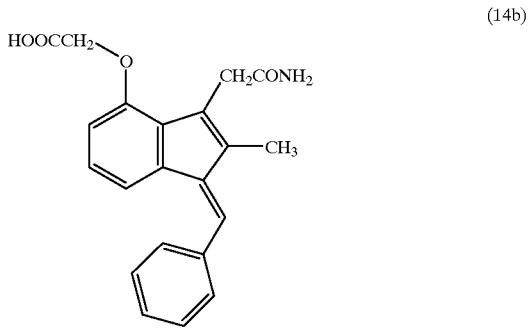

(14b)

The salts of the above indene-1-functional compounds represented by formulae (I), (II), (III) are an additional aspect of the invention. In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: pp. 1–19 (1977)). Moreover, the basic group (s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans- isomeric forms of the compounds. The R- and S- isomers and mixtures thereof, including racemic mixtures as well as mixtures of cis- and trans- isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods.

Prodrugs are derivatives of the compounds of the invention which have chemically or metabolically cleavable groups and become by solvolysis or under physiological conditions the compounds of the invention which are pharmaceutically active in vivo. The prodrug derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters.

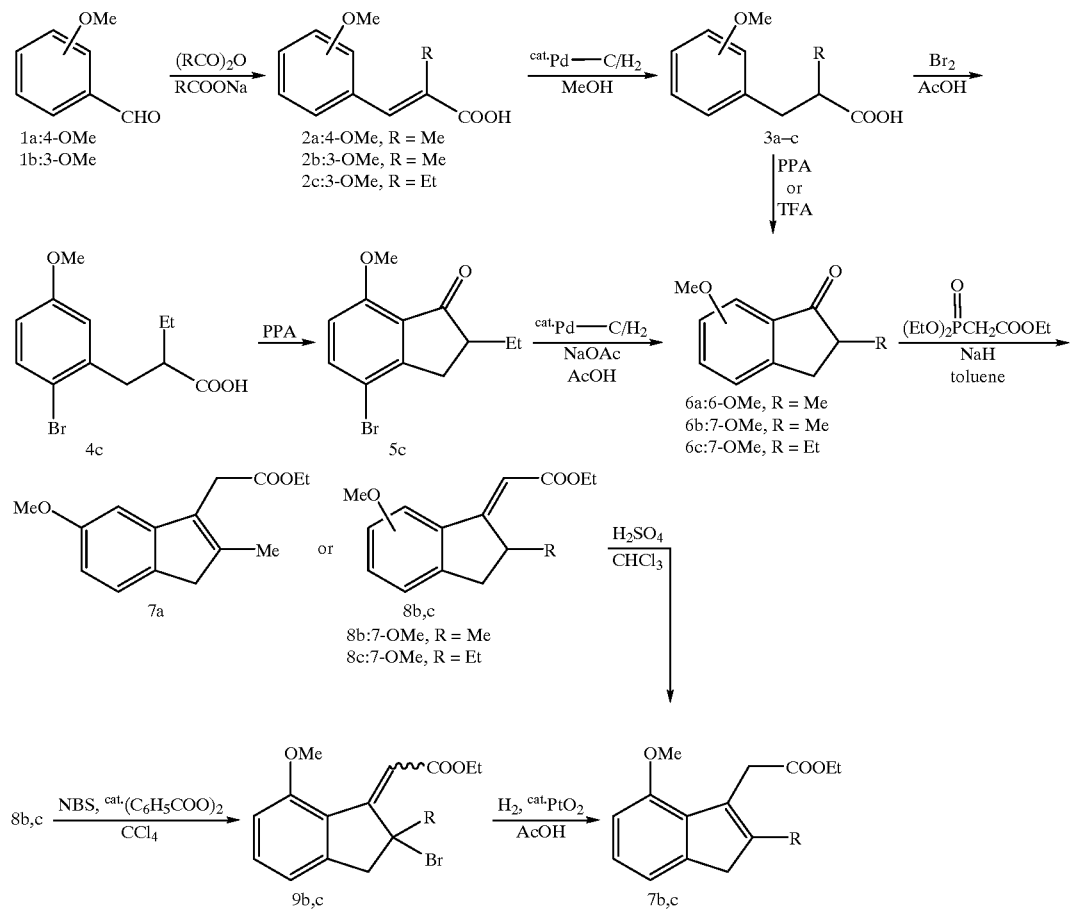

Synthesis Methods
Scheme 1

A mixture of an anisaldehyde 1, propionic anhydride, and sodium propionate is heated to produce 2 which is reduced by hydrogen in the presence of Pd/C to give 3. Acid cyclization of 3 yields 6. Alternatively, the aromatic position para to the methoxy group of 3 is blocked by bromination to give 4 which is cyclized to 5 by acid and then debrominated using hydrogen and Pd/c to give 6. Reaction of 6 with the anion of triethyl phosphonoacetate produces 7 and/or 8. Radical bromination of 8 gives 9, which on reduction with hydrogen in the presence of PtO$_2$ yields 7. Alternatively, treatment of 8 with acid gives 7.

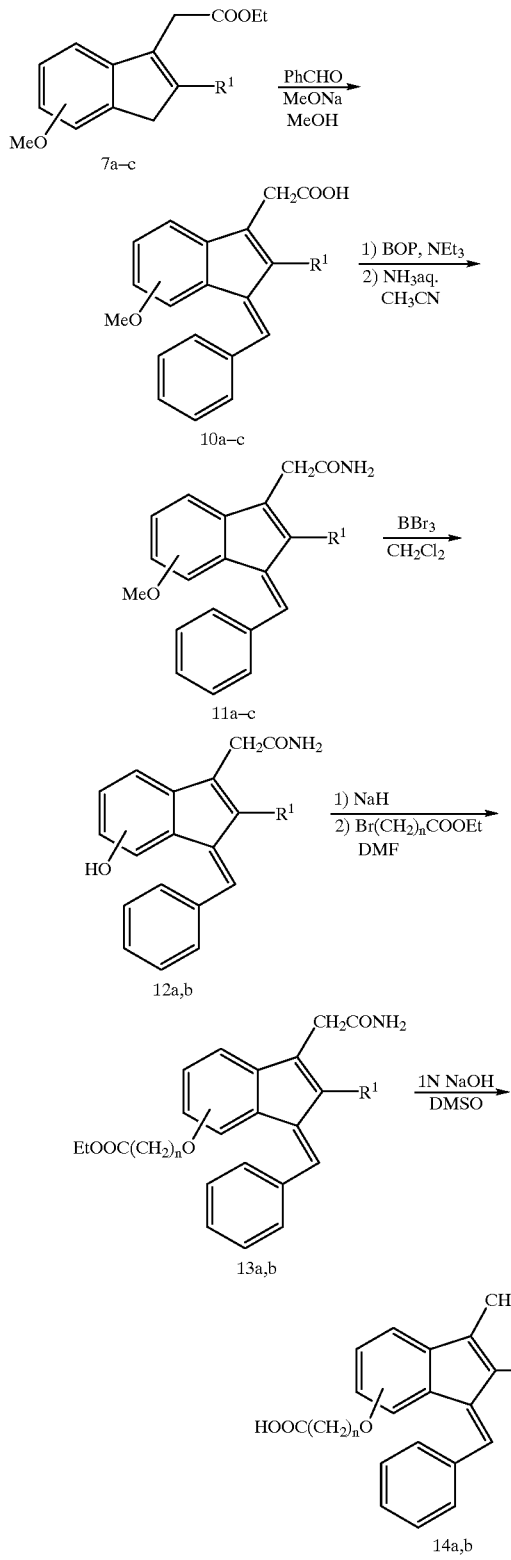

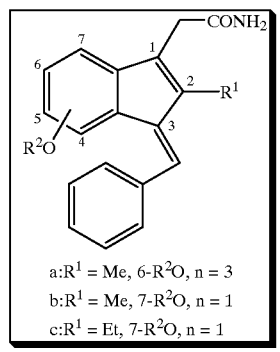

a: R$^1$ = Me, 6-R$^2$O, n = 3
b: R$^1$ = Me, 7-R$^2$O, n = 1
c: R$^1$ = Et, 7-R$^2$O, n = 1

Compound 7 is condensed with benzaldehyde in the presence of base to give 10. Indenes 10 are converted to an active ester using benzotriazo-1-yloxytris(dimethylamino) hexafluorophosphonate and the reacted with ammonium hydroxide to form 11. Demethylation of 11 with BBr$_3$ forms 12 which is O-alkylated using sodium hydride and a omega-bromoalkanoic acid ester to produce 13. Aqueous base hydrolysis of 13 yields 14.

EXAMPLES

Reference numbers in the following Examples refer to compounds shown in the preceding Schemes.

Example 1

Preparation of 4-[3(z)-benzylidene-1-carbamoylmethyl-2-methyl-3H-inden-6-yloxy]-butanoic acid 14a, a compound represented by the formula:

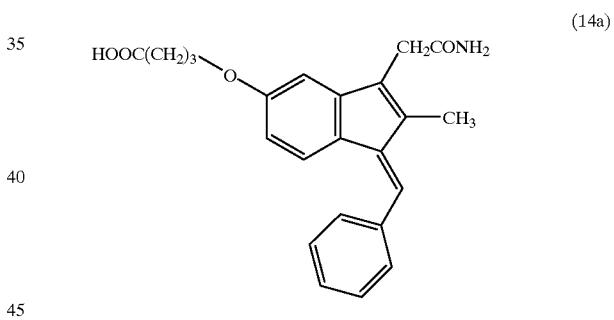

(14a)

and [3(z)-benzylidene-1-carbamoylmethyl-2-methyl-3H-inden-7-yloxy]-acetic acid 14b, a compound represented by the formula:

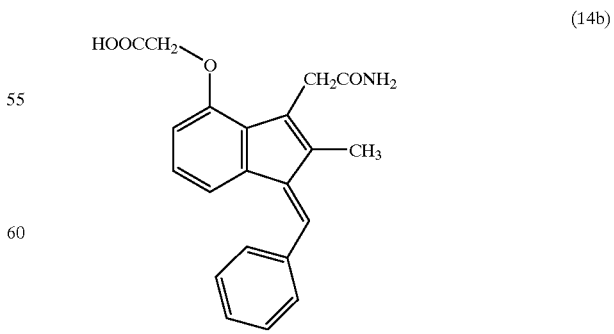

(14b)

Part A: Preparation of 3-(4-methoxyphenyl)-2-methyl-acrylic acid 2a

A mixture of p-anisaldehyde (26.6 g, 0.195 mol), propionic anhydride (43.0 ml, 0.347 mol) and sodium propionate (18.8 g, 0.195 mol) was heated at 150° C. overnight. After cooling, the reaction mixture was basified with 4N NaOH and washed with ether. The aqueous phase was acidified with conc.HCl and the precipitate was filtered to yield 28.5 g (76%) of the titled compound, mp, 152–155° C.

$^1$H NMR (CDCl$_3$) δ 2.16 (3H, d, J=1.2 Hz), 3.85 (3H, s), 6.95 (2H, d, J=8.7 Hz), 7.44 (2H, d, J=8.7 Hz), 7.78 (1H, br.s). IR $v_{max}$ (KBr) 1662, 1605, 1570, 1510 cm$^{-1}$, EIMS m/z=192 (M+, base peak). Analyses for C$_{11}$H$_{12}$O$_3$: Calculated: C, 68.74; H, 6.29. Found: C, 68.49; H, 6.38.

3-(3-methoxyphenyl)-2-methyl-acrylic acid 2b Mp, 78–79° C. 93% yield.

$^1$H NMR (CDCl$_3$) δ 2.15 (3H, d, J=1.2 Hz), 3.84 (3H, s), 6.99–6.85 (2H, m), 7.03 (1H, d, J=8.0 Hz), 7.34 (1H, t, J=8.0 Hz), 7.81 (1H, s). IR $v_{max}$ (KBr) 3434, 2997, 2969, 2942, 2835, 1666, 1606, 1576, 1495 cm$^{-1}$. EIMS m/z=192 (base peak, M+) Analyses for C$_{11}$H$_{12}$O$_3$: Calculated: C, 68.74; H, 6.29. Found: C, 68.48; H, 6.30.

2-ethyl-3-(3-methoxyphenyl)-acrylic acid 2c Mp, 89–90° C. 24% yield.

$^1$H NMR (CDCl$_3$) δ 1.22 (3H, s), 2.58 (2H, s), 3.84 (3H, s), 6.85–6.97 (2H, m), 7.01 (1H, d, J=7.4 Hz), 7.33 (1H, t, J=7.8 Hz), 7.77 (1H, s). IR $v_{max}$ (KBr) 3431, 2984, 2968, 2934, 2873, 2840, 1674, 1622, 1603, 1576, 1491 cm$^{-1}$. EIMS m/z=206 (base peak, M+). Analyses for C$_{12}$H$_{14}$O$_3$: Calculated: C, 69.89; H, 6.84. Found: C, 69.80; H, 6.86.

Part B: Preparation of 3-(4-methoxyphenyl)-2-methyl-propionic acid 3a

A mixture of the acrylic acid (2a, 28.3 g, 0.147 mol) and 10% palladium-coal (2.49 g) in methanol (350 ml) was hydrogenated under 3 atm overnight. The catalyst was filtered off and the solvent was evaporated to give the desired product (21.2 g, 74%). mp, 43–44° C.

$^1$H NMR (CDCl$_3$) δ 1.17 (3H, d, J=6.8 Hz), 2.54–2.83 (2H, m), 3.01 (1H, dd, J=5.4, 12.4 Hz), 3.79 (3H, s), 6.83 (2H, d, J=8.7 Hz), 7.10 (2H, d, J=8.7 Hz). IR $v_{max}$ (film) 3424, 2970, 2933, 2838, 1709, 1612, 1584, 1513, 1465 cm$^{-1}$. Analyses for C$_{11}$H$_{14}$O$_3$: Calculated: C, 68.02; H, 7.26. Found: C, 67.72; H, 7.28.

3-(3-methoxyphenyl)-2-methyl-propionic acid 3b

Using the procedure described in the synthesis of compound 3a from 2a, the acrylic acid (7, 38.2 g, 0.199 mol), was hydrogenated under atmospheric pressure to give the desired product (29.0 g, 75%).

$^1$H NMR (CDCl$_3$) δ 1.19 (3H, d, J=6.6 Hz), 2.57–2.89 (2H, m), 3.06 (1H, dd, J=12.7, 6.1 Hz), 3.79 (3H, s), 6.71–6.83 (3H, m), 7.21 (1H, t, J=7.8 Hz) IR $v_{max}$ (film) 2974, 2938, 2836, 1706, 1602, 1585, 1490, 1464 cm$^{-1}$. EIMS m/z=121 (base peak), 194 (M+). Analyses for C$_{11}$H$_{14}$O$_3$ 0.1H$_2$O: Calculated: C, 67.40; H, 7.30. Found: C, 67.66; H, 7.25.

2-(3-methoxybenzyl)-butyric acid 3c Quantitive yield.

$^1$H NMR (CDCl$_3$) δ 0.96 (3H, t, J=7.4 Hz), 1.50–1.76 (2H, m), 2.52–2.80 (2H, m), 2.97 (1H, dd, J=13.2, 7.4 Hz), 3.78 (3H, s), 6.70–6.82 (3H, m), 7.19 (1H, td, J=7.4, 1.2 Hz). IR $v_{max}$ (film) 2964, 2937, 2877, 2836, 1705, 1602, 1585, 1490, 1458, 1437 cm$^{-1}$. EIMS m/z=122 (base peak), 208 (M+). Analyses for C$_{12}$H$_{16}$O$_3$: Calculated: C, 69.21 H, 7.74. Found: C, 69.05; H, 7.82.

Part C: Preparation of 2-(2-bromo-5-methoxy-benzyl)-butyric acid 4c

To a solution of the butyric acid (3a, 33.9 g, 0.163 m mol) in acetic acid (50 ml) was added a solution of bromine (10.5 ml, 0.204 m mol) in acetic acid (20 ml) at 0° C. The resulting orange solution was stirred at room temperature for 2.5 hours and the mixture was partitioned between water and AcOEt. The aqueous layer was extracted with AcOEt and the combined organic layers were washed with saturated sodium thiosulfate solution, water and brine, dried over MgSO$_4$, filtered and evaporated in vacuo. The residue (14, 51.8 g) was used to the next preparation without further purification, mp, 39–42° C.

$^1$H NMR (CDCl$_3$) δ 1.00 (3H, t, J=7.4 Hz), 1.55–1.83 (2H, m), 2.68–3.08 (3H, m), 3.75 (3H, s), 6.65 (1H, dd, J=8.8, 3.0 Hz), 6.78 (1H, d, J=3.0 Hz), 7.41 (1H, d, J=8.8 Hz). IR $v_{max}$ (KBr) 3010, 2962, 2941, 2877, 1689, 1593, 1577 cm$^{-1}$.

Part D: Preparation of 4-bromo-2-ethyl-7-methoxy-1-indanone 5c

A mixture of the butyric acid (4c, 51.6 g) and polyphosphoric acid (511 g) was heated at 100° C. for 2.5 hours. The mixture was poured into water (1 L) and extracted with AcOEt. The combined extracts were washed with water, 5% sodium bicarbonate solution and brine, dried over MgSO$_4$ and filtered. After removing the solvent under reduced pressure, the residue was chromatographed on silica gel eluting with hexane:AcOEt (4:1 to 1:2) to give the titled compound (30.0 g).

$^1$H NMR (CDCl$_3$) δ 1.02 (3H, s, J=7.4 Hz), 1.40–1.66 (1H, m), 1.85–2.10 (1H, m), 2.52–2.76 (2H, m), 3.19 (1H, dd, J=18.2, 8.0 Hz), 3.94 (3H, s), 6.72 (1H, d, J=8.8 Hz), 7.64 (1H, d, J=8.8 Hz). IR $v_{max}$ (film) 2960, 2933, 2872, 2840, 1712, 1585, 1474, 1436 cm$^{-1}$. EIMS m/z=240 (base peak), 268 (M+).

Part E-1: Preparation of 6-methoxy-2-methyl-1-indanone 6a

To the propionic acid (3a, 21.0 g, 0.108 mol) was added polyphosphoric acid (abt. 200 g) at 50° C., the reaction was maintained at 90° C. for 2 hours. The mixture was poured into water (1 L), stirred at room temperature overnight and extracted with ether twice. The combined extracts were washed with saturated sodium bicarbonate solution and brine, dried over MgSO$_4$ and filtered. After removing the solvent under reduced pressure, the residue was chromatographed on silica gel eluting with CH$_2$Cl$_2$:MeOH (10:0 to 9:1) and hexane:AcOEt (9:1 to 10:1) to give the titled compound (7.45 g, 39%).

$^1$H NMR (CDCl$_3$) δ 1.31 (3H, d, J=7.2 Hz), 2.58–2.84 (2H, m), 3.33 (1H, dd, J=16.1, 7.1 Hz), 3.84 (3H, s), 7.15–7.23 (2H, m), 7.30–7.40 (1H, m).

Part E-2: Preparation of 7-methoxy-2-methyl-1-indanone 6b

To a solution of the propionic acid (3b, 17.4 g, 0.0897 m mol) in trifluoroacetic acid (300 ml) was slowly added trifluoroacetic anhydride (70 ml) at 0° C. and the reaction was maintained at this temperature for 40 min. After removing the solvent, the residue was dissolved with ether and poured into 10% NaOH. The organic layer was separated and washed with 10% NaOH, water and brine. The aqueous layer was extracted with ether and the combined extracts were dried over MgSO$_4$, filtered and concentrated in vacuo. The residue was chromatographed on silica gel eluting with hexane:AcOEt (9:1 to 1:1) to give the titled compound (2.66 g, 17%).

$^1$H NMR (CDCl$_3$) δ 1.29 (3H, d, J=7.0 Hz), 2.58–2.79 (2H, m), 3.33 (1H, dd, J=8.6, 18.0 Hz), 3.95 (3H, s), 6.78 (1H, d, J=8.2 Hz), 6.99 (1H, d, J=7.4 Hz), 7.52 (1H, t, J=8.0 Hz). IR $v_{max}$ (film) 2962, 2931, 2871, 2840, 1705, 1597, 1480 cm$^{-1}$. EIMS m/z=176 (base peak, M+). Analyses for C$_{11}$H$_{12}$O$_2$ 0.1H$_2$O: Calculated: C, 74.22; H, 6.91. Found: C, 74.16; H, 6.90.

Part E-3: Preparation of 2-ethyl-7-methoxy-1-indanone 6c

A mixture of the indanone (5c, 29.7 g, 0.110 mol), sodium acetate (15.0 g, 0.183 mol), 10% palladium-coal (3.01 g) in acetic acid (300 ml) was hydrogenated at atmospheric pressure. The catalyst was filtered off and the solvent evaporated. The residue was partitioned between water and AcOEt and the aqueous layer was extracted with AcOEt. The combined organic layers were washed with water, 5% $NaHCO_3$ and brine, dried, filtered and evaporated. The crude product was purified by recrystallization from hexane:AcOEt to give the pure titled compound (15.7 g, 3 steps yield 51%), mp, 67–69° C.

$^1$H NMR (CDCl$_3$) δ 1.00 (3H, t, J=7.3 Hz), 1.38–1.63 (1H, m), 1.85–2.08 (1H, m), 2.50–2.66 (1H, m), 2.76 (1H, dd, J=17.4, 4.0 Hz), 3.25 (1H, dd, J=17.4, 7.9 Hz), 3.95 (1H, s), 6.78 (1H, d, J=8.2 Hz), 7.00 (1H, d, J=7.5 Hz), 7.51 (1H, t, J=7.8 Hz). IR $v_{max}$ (KBr) 2955, 2932, 2899, 1703, 1593, 1483 cm$^{-1}$ EIMS m/z=162 (base peak), 190 (M+). Analyses for $C_{12}H_{14}O_2$: Calculated: C, 75.76; H, 7.42. Found: C, 75.50; H, 7.42.

Part F: Preparation of ethyl (6-methoxy-2-methyl-3H-indene-1-yl)-acetate 7a

To a solution of triethyl phosphonoacetate (17.2 g, 76.7 m mol) in toluene (100 ml) was added sodium hydride (60% oil suspension, 3.06 g, 76.5 m mol) at 0° C. After the reaction mixture was stirred for 1 hour at this temperature, a solution of the indanone (6a, 1.35 g, 7.63 m mol) in toluene (25 ml) was slowly added. The mixture was refluxed for 4 hours, then was poured into 1N HCl and extracted with AcOEt. The extract was washed with water and brine, dried over $MgSO_4$, filtered and concentrated to produce a crude residue, which was chromatographed on silica gel eluting with hexane:AcOEt (19:1) to give the mixture of the compound 7a and its positional isomer (1.65 g, 88%). The mixture was used to the next preparation without further purification.

$^1$H NMR (CDCl$_3$) δ 1.24 (3H, t, J=7.2 Hz), 2.12 (3H, s), 3.27 (2H, s), 3.49 (2H, s), 3.83 (3H, s), 4.14 (2H, q, J=7.2 Hz), 6.68 (1H, dd, J=2.5, 8.1 Hz), 6.86 (1H, d, J=2.5 Hz), 7.24 (1H, d, J=8.1 Hz).

Note: For the preparation of compounds 7b and 7c, see Part I, infra.

Part G-1: Preparation of ethyl (7-methoxy-2-methyl-inden-1-ylidene)-acetate 8b

To a solution of triethyl phosphonoacetate (12.7 g, 56.7 m mol) in toluene (100 ml) was added sodium hydride (60% oil suspension, 2.29 g, 57.3 m mol) at 0° C. After the reaction mixture was stirred for 70 min at this temperature, a solution of the indanone (6b, 2.00 g, 11.4 m mol) in toluene (28 ml) was added. The mixture was refluxed for overnight, then was poured into 2N HCl and extracted with AcOEt. The extract was washed with water and brine, dried over $MgSO_4$, filtered and concentrated to produce a crude residue, which was chromatographed on silica gel eluting with hexane:AcOEt (9:1) to give the titled compound (1.36 g, 49%).

$^1$H NMR (CDCl$_3$) δ 1.24 (3H, d, J=6.6 Hz), 1.27 (3H, t, J=7.0 Hz), 2.50–2.71 (1H, m), 2.93–3.19 (2H, m), 3.81 (3H, s), 4.21 (2H, q, J=7.0 Hz), 5.81 (1H, d, J=2.0 Hz), 6.70 (1H, d, J=8.4 Hz), 6.86 (1H, d, J=7.6 Hz), 7.25 (1H, t, J=7.8 Hz).

Part G-2: Preparation of ethyl (2-ethyl-7-methoxyindan-1-ylidene)-acetate 8c 36% yield.

$^1$H NMR (CDCl$_3$) δ 0.98 (3H, t, J=7.2 Hz), 1.27 (3H, t, J=7.2 Hz), 1.34–1.80 (2H, m), 2.64 (1H, dd, J=15.3, 4.7 Hz), 2.77–2.93 (1H, m) , 3.13 (1H, dd, J=15.3, 7.3 Hz), 3.81 (3H, s), 4.21 (2H, q, J=7.2 Hz), 5.84 (1H, d, J=1.6 Hz), 6.69 (1H, d, J=8.2 Hz), 6.87 (1H, dd, J=7.4, 0.8 Hz), 7.25 (1H, t, J=7.8 Hz). IR $v_{max}$ (film) 3063, 2961, 2934, 2874, 2839, 1718, 1643, 1598, 1585, 1482, 1463 cm$^{-1}$. Analyses for $C_{16}H_{20}O_3$ 0.1$H_2O$: Calculated: C, 73.31; H, 7.77. Found: C, 73.41; H, 7.72.

Part H-1: Preparation of ethyl (2-bromo-7-methoxy-2-methyl-indan-1-ylidene)-acetate 9b To a solution of the ester compound (8a, 1.39 g, 5.65 m mol) in carbon tetrachloride (15 ml) were added N-bromosuccinimide (1.11 g, 6.22 m mol) and benzoyl peroxide (68.5 mg, 0.283 m mol). The mixture was stirred at 50° C. for 6 hours, filtered, washed with saturated sodium thiosulfate solution and dried. After removing the solvent, the residue was chromatographed on silica gel eluting with hexane:AcOEt (19:1) to afford the titled compound (0.424 g, 23%), mp, 85–91° C.

$^1$H NMR (CDCl$_3$) δ 1.23 (3H, t, J=7.2 Hz), 2.12 (3H, s), 3.42 (2H, s), 3.84 (3H, s), 4.22 (2H, qd, J=7.2, 1.0 Hz), 6.02 (1H, s), 6.79 (1H, d, J=8.0 Hz), 7.01 (1H, dd, J=7.2, 0.8 Hz), 7.13 (1H, t, J=7.7 Hz). IR $v_{max}$ (KBr) 3435, 3063, 2956, 2939, 2908, 2837, 1750, 1611, 1580 cm$^{-1}$. EIMS m/z=199 (base peak), 324 (M+).

Part H-2: Preparation of ethyl (2-bromo-2-ethyl-7-methoxy-indan-1-ylidene)-acetate 9c The ester compound (8c, 2.46 g, 9.44 m mol) in carbon tetrachloride (30 ml) was reacted with N-bromosuccinimide (2.03 g, 11.4 m mol) and benzoyl peroxide (0.116 g, 0.48 m mol) to give the crude product. This compound was used to the next step without purification.

Part I-1: Preparation of ethyl (7-methoxy-2-methyl-3H-inden-1-yl)-acetate 7b (see, Part F, supra, for preparation of compound 7a).

The mixture of the ester compound (9b, 388 mg, 1.19 m mol) and platinum dioxide (38.4 mg) in acetic acid (4.0 ml) was hydrogenated under ordinary atmosphere overnight. The catalyst was filtered off and the solvent was evaporated. The residue was chromatographed on silica gel eluting with hexane:AcOEt (97:3 to 9:1) and crystallized from hexane:AcOEt to give 170 mg (59%) of the titled compound, mp, 76–79° C.

$^1$H NMR (CDCl$_3$) δ 1.25 (3H, s, J=7.0 Hz), 2.04 (3H, s), 3.32 (2H, s), 3.67 (2H, s), 3.78 (3H, s), 4.16 (2H, q, J=7.0 Hz), 6.73 (1H, d, J=7.8 Hz), 6.98 (1H, d, J=6.6 Hz), 7.06 (1H, t, J=7.7 Hz). IR $v_{max}$ (KBr) 3448, 3062, 2980, 2937, 2908, 2840, 1735, 1634, 1578 cm$^{-1}$. EIMS m/z=172 (base peak), 246 (M+). Analyses for $C_{15}H_{18}O_3$ 0.1$H_2O$: Calculated: C, 72.62; H, 7.39. Found: C, 72.48; H, 7.37.

Part I-2: Preparation of ethyl (2-ethyl-7-methoxy-3H-inden-1-yl)-acetate 7c

To a solution of the ester compound (8c, 4.15 g, 0.0160 mol) in chloroform (40 ml) were added three drops of concentrated sulfuric acid. The resulting solution was refluxed for 40 minutes, dried over $K_2CO_3$ and filtered. After removing the solvent under reduced pressure, the residue was chromatographed on silica gel eluting with hexane:AcOEt (98:2 to 95:5) to give 7c (3.55 g, 85% yield).

$^1$H NMR (CDCl$_3$) δ 1.14 (3H, t, J=7.6 Hz), 1.25 (3H, t, J=7.0 Hz), 2.44 (2H, q, J=7.6 Hz), 3.36 (2H, s), 3.68 (2H, s), 3.79 (3H, s), 4.15 (2H, q, J=7.0 Hz), 6.62–6.85 (1H, m), 6.97–7.18 (2H, m). IR $v_{max}$ (film) 3384, 2966, 2936, 2836, 1736, 1678, 1612, 1593, 1583, 1481, 1464, 1442 cm$^{-1}$. Analyses for $C_{16}H_{20}O_3$ 0.5$H_2O$: Calculated: C, 71.35; H, 7.86. Found: C, 71.46; H, 7.55.

Part J: Preparation of [(3Z)-benzylidene-6-methoxy-2-methyl-3H-inden-1-yl]-acetic acid 10a To a solution of the crude indene (7a, 1.64 g, 6.66 m mol) in methanol (20 ml) were added benzaldehyde (1.35 ml, 13.3 m mol) and 1N NaOMe (20.0 ml, 20 m mol) at room temperature. The resulting solution was refluxed for 160 min, evaporated, poured into 1N HCl and extracted with AcOEt. The organic layer was washed with water and brine, dried over $MgSO_4$, filtered and concentrated in vacuo. The residue was subjected successively to chromatography on silica gel eluting with hexane:AcOEt (9:1) and then CHCl$_3$:MeOH (9:1) and to recrystallization (hexane:AcOEt) to afford 0.841 g (41% yield) of the desired product 10a, mp, 146–160° C.

$^1$H NMR (CDCl$_3$) δ 2.19 (3H, s), 3.59 (2H, s), 3.78 (3H, s), 6.40 (1H, dd, J=8.2, 2.4 Hz), 6.75 (1H, d, J=2.4 Hz), 7.12 (1H, s), 7.24 (1H, d, J=8.2 Hz), 7.30–7.56 (5H, m). IR ν$_{max}$ (KBr) 3428, 3007, 2935, 2834, 1701, 1611, 1582 cm$^{-1}$. EIMS m/z=306 (M+, base peak). Analyses for C$_{20}$H$_{18}$O$_3$ 0.2H$_2$O: Calculated: C, 77.50; H, 5.98. Found: C, 77.35; H, 5.97.

[3(Z)-benzyliden-7-methoxy-2-methyl-3H-inden-1-yl]-acetic acid 10b Mp, 165–175° C. 59% yield.

$^1$H NMR (CDCl$_3$) δ 2.14 (3H, s), 3.79 (3H, s), 3.81 (2H, s), 6.70 (1H, dd, J=8.2, 0.8 Hz), 6.82 (1H, t, J=7.8 Hz), 6.98 (1H, dd, J=7.5, 0.8 Hz), 7.22 (1H, s), 7.33–7.56 (5H, m). IR ν$_{max}$ (KBr) 3425, 3081, 3049, 3004, 2937, 1705, 1598, 1578 cm$^{-1}$. EIMS m/z=306 (base peak, M+). Analyses for C$_{20}$H$_{18}$O$_3$ 0.6H$_2$O: Calculated: C, 75.74; H, 6.10. Found: C, 75.86; H, 6.01.

[(3Z)-benzylidene-2-ethyl-7-methoxy-3H-inden-1-yl]-acetic acid 10c Decomp, 166–188° C. 47% yield.

$^1$H NMR (CDCl$_3$) δ 1.93 (3H, t, J=7.7 Hz), 2.59 (2H, q, J=7.7 Hz), 3.80 (5H, s), 6.72 (1H, dd, J=8.1, 0.8 Hz), 6.84 (1H, t, J=7.9 Hz), 7.00 (1H, dd, J=7.5, 0.8 Hz), 7.25 (1H, s), 7.31–7.57 (5H, m). IR ν$_{max}$ (KBr) 3423, 2967, 2936, 1708, 1597, 1578, 1481 cm$^{-1}$. Analyses for C$_{21}$H$_{20}$O$_3$ 0.4H$_2$O: Calculated: C, 77.00; H, 6.40. Found: C, 76.94; H, 6.40.

Part K: Preparation of 2-[3(Z)-benzylidene-6-methoxy-2-methyl-3H-inden-1-yl]-acetamide 11a To a solution of the acetic acid derivatve (10a, 200 mg, 0.645 m mol) in acetonitrile (10.0 ml) were added triethylamine (0.140 ml, 1.00 m mol) and benzotriazol-1-yloxytris (dimethylamino)phosphonium hexafluorophosphonate (434 mg, 0.981 m mol) at 0° C. The resulting solution was stirred at room temperature for 45 min, and then 28% aqueous ammonia (0.440 ml) was added. After 30 min, the mixture was poured into 2N HCl and extracted with AcOEt. The organic layer was washed with water and brine, dried over MgSO$_4$ and filtered. After removing the solvent at reduced pressure, the residue was chromatographed twice on silica gel eluting with CH$_2$Cl$_2$:MeOH (99:1 to 98.5:1.5) and hexane:AcOEt (1:1 to 1:9) to give 183 mg (92%) of the titled compound, mp, 174–178° C.

$^1$H NMR (CDCl$_3$) δ 2.22 (3H, s), 3.55 (2H, s), 3.79 (3H, s), 5.44 (1H, br.s), 5.64 (1H, br.s), 6.44 (1H, dd, J=8.4, 2.4 Hz), 6.73 (1H, d, J=2.4 Hz), 7.16 (1H, s), 7.29 (1H, d, J=8.4 Hz), 7.32–7.60 (5H, m). IR ν$_{max}$ (KBr) 3389, 3196, 2913, 1653, 1614 cm$^{-1}$. EIMS m/z=305 (M+, base peak). Analyses for C$_{20}$H$_{19}$NO$_2$ 0.3H$_2$O: Calculated: C, 77.30; H, 6.36; N, 4.51. Found: C, 77.18; H, 6.35; N, 4.40.

2-[3(Z)-benzilidene-7-methoxy-2-methyl-3H-inden-1-yl]-acetamide 11b Mp, 175–177° C. 96% yield.

$^1$H NMR (d$_6$-DMSO) δ 2.06 (3H, s), 3.54 (2H, s), 3.75 (3H, s), 6.70–6.95 (4H, m), 7.06 (1H, br.s), 7.28 (1H, s), 7.32–7.60 (5H, m). IR ν$_{max}$ (KBr) 3510, 3448, 3400, 3177, 3060, 3023, 2942, 2838, 1698, 1667, 1595, 1574 cm$^{-1}$. EIMS m/z=305 (base peak, M+).

2-[(3Z)-benzylidene-2-ethyl-7-methoxy-3H-inden-1-yl]-acetamide 11c Mp, 153–156° C. 71% yield.

$^1$H NMR (CDCl$_3$) δ 1.21 (3H, t, J=7.6 Hz), 2.64 (2H, q, J=7.6 Hz), 3.74 (2H, s), 3.86 (3H, s), 5.25 (1H, br.s), 5.98 (1H, br.s), 6.76 (1H, d, J=7.8 Hz), 6.87 (1H, t, J=7.8 Hz), 7.02 (1H, d, J=7.0 Hz), 7.28 (1H, s), 7.31–7.56 (5H, m).

Part L: Preparation of 2-[3(Z)-benzylidene-6-hydroxy-2-methyl-3H-inden-1-yl]-acetamide 12a To a solution of the acetamide (11a, 50.9 mg, 0.167 m mol) in dichloromethane (2.0 ml) was added dropwise borontribromide (1M in CH$_2$Cl$_2$ solution, 0.860 ml, 0.860 m mol) at 0° C. and the resulting mixture was stirred at room temperature for 80 min. After evaporation, methanol (2.0 ml) was added. The solution was stirred and evaporated. The residue was partitioned between 2N HCl and AcOEt, the extract was washed with water and brine, dried over MgSO$_4$ and concentrated in vacuo. The crude product was purified by preparative TLC on silica gel (200 mm×200 mm×0.25 mm, elution with AcOEt) and recrystallization from hexane:AcOEt to afford the titled compound (23.7 mg, 49%), mp, 178–180° C.

$^1$H NMR (CDCl$_3$) δ 2.20 (3H, s), 3.56 (2H, s), 5.55 (1H, br.s), 5.77 (1H, br.s), 6.41 (1H, d, J=8.4, 2.4 Hz), 6.69 (1H, d, J=2.4 Hz), 7.14 (1H, s), 7.25 (1H, d, J=8.4 Hz), 7.30–7.56 (6H, m) IR ν$_{max}$ (KBr) 3416, 3212, 1657, 1602 cm$^{-1}$. EIMS m/z=232 (base peak), 291 (M+). Analyses for C$_{19}$H$_{17}$NO$_2$ 0.4H$_2$O: Calculated: C, 76.44; H, 6.01; N, 4.69. Found: C, 76.66; H, 5.91; N, 4.63.

2-[3(Z)-benzylidene-7-hydroxy-2-methyl-3H-inden-1-yl]-acetamide 12b Mp, 200–203° C. Quantitative yield.

$^1$H NMR (CD$_3$OD) δ 2.16 (3H, s), 3.72 (2H, s), 6.55–6.74 (2H, m), 6.83 (1H, dd, J=7.0, 1.6 Hz), 7.22 (1H, s), 7.28–7.54 (5H, m) EIMS m/z=274 (base peak), 291 (M+).

Part M-1: Preparation of ethyl 4-[3(Z)-benzylidene-1-carbamoylmethyl-2-methyl-3H-inden-6-yloxy]-butanoate 13a To a solution of the hydroxy compound (12a, 43.7 mg, 0.150 m mol) in dimethylformamide (1.0 ml) was added sodium hydride (60% oil suspension, 21.3 mg, 0.533 m mol). After addition, the mixture was stirred at room temperature for 60 min, and then ethyl 4-bromobutyrate (75 μl, 0.524 m mol) was added. The mixture was stirred at 0° C. for 45 min and then at room temperature for 75 min, and partitioned between 1N HCl and AcOEt. The organic layer was separated, washed with water and brine, dried over MgSO$_4$, filtered and concentrated in vacuo. The residue was purified by preparative TLC (200 mm×200 mm×0.25 mm, elution with AcOEt) to give the product (38.0 mg, 63%), mp, 124–128° C.

$^1$H NMR (CDCl$_3$) δ 1.25 (3H, t, J=7.0 Hz), 1.99–2.17 (2H, m), 2.21 (3H, s), 2.50 (2H, t, J=7.2 Hz), 3.54 (2H, s), 3.98 (2H, t, J=6.3 Hz), 4.14 (2H, q, J=7.0 Hz), 5.50 (1H, br.s), 5.67 (1H, br.s), 6.42 (1H, dd, J=8.2, 2.4 Hz), 6.73 (1H, d, J=2.4 Hz), 7.16 (1H, s), 7.27 (1H, d, J=8.2 Hz), 7.32–7.58 (5H, m). IR ν$_{max}$ (KBr) 3445, 2972, 2919, 1739, 1687, 1655, 1614 cm$^{-1}$. EIMS m/z=115 (base peak), 405 (M+). Analyses for C$_{25}$H$_{27}$NO$_4$ 0.9H$_2$O: Calculated: C, 71.20; H, 6.88; N, 3.32 Found: C, 71.13; H, 6.76; N, 3.52.

Part M-2: Preparation of ethyl [3(Z)-benzylidene-1-carbamoylmethyl-2-methyl-3H-inden-7-yloxy]-acetate 13b Using the procedure described in the synthesis of compound 13a from 12a, the hydroxy compound (21b, 53.1 mg, 0.182 m mol) in dimethylformamide (1.0 ml) was reacted with sodium hydride (60% oil suspension, 26.1 mg, 0.653 m mol) and ethyl bromoacetate (72 μl, 0.649 m mol). Purification by preparative TLC (200 mm×200 mm×0.25 mm, elution with CHCl$_3$:MeOH (19:1)) gave the product (53.1 mg, 77%), mp, 162–165° C.

$^1$H NMR (CDCl$_3$) δ 1.33 (3H, t, J=7.2 Hz), 2.26 (3H, s), 3.82 (2H, s), 4.30 (2H, q, J=7.2 Hz), 4.68 (2H, s), 5.26 (1H, br.s), 6.60 (1H, d, J=8.2 Hz), 6.81 (1H, t, J=8.0 Hz), 6.92 (1H, br.s), 7.03 (1H, d, J=7.4 Hz), 7.26 (1H, s), 7.30–7.57 (5H, m). IR ν$_{max}$ (KBr) 3401, 3164, 3001, 2981, 2933, 1740, 1685, 1597, 1575 cm$^{-1}$. EIMS m/z=377 (base peak, M+). Analyses for C$_{23}$H$_{23}$NO$_4$ 0.8H$_2$O: Calculated: C, 70.50; H, 6.33; N, 3.57. Found: C, 70.49; H; 6.07; N, 3.62.

Part N-1: Preparation of 4-[3(Z)-benzylidene-1-carbamoylmethyl-2-methyl-3H-inden-6-yloxy]-butanoic acid 14a 1N Sodium hydroxide (0.200 ml, 0.200 m mol) was added to a solution of the ester (13a, 39.4 mg, 0.0972 m mol) in dimethylsulfoxide (1.0 ml) at room temperature. The solution was stirred at room temperature for 75 min, partitioned between 1N HCl and AcOEt. The organic layer was separated, washed with water and brine, dried over $MgSO_4$, filtered and evaporated in vacuo. Recrystallization from AcOEt afforded the titled compound (19.5 mg, 53%), mp, 187–188° C.

$^1$H NMR ($d_6$-DMSO) δ 1.82–2.02 (2H, m), 2.14 (3H, s), 2.36 (2H, t, J=7.0 Hz), 3.94 (1H, t, J=6.3 Hz), 6.42 (1H, dd, J=8.4, 2.0 Hz), 6.85 (1H, d, J=2.0 Hz), 6.96 (1H, br.s), 7.13 (1H, d, J=8.4 Hz), 7.16 (1H, s), 7.32–7.57 (6H, m). IR $v_{max}$ (KBr) 3462, 3342, 3190, 2936, 1715, 1697, 1647, 1613, 1582 cm$^{-1}$. EIMS m/z=232 (base peak), 377 (M+). Analyses for $C_{23}H_{23}NO_4$ 0.5$H_2O$: Calculated: C, 71.49; H, 6.26; N, 3.62. Found: C, 71.47; H, 6.25; N, 3.47.

Part N-2: Using the procedure described in the synthesis of compound 14a from 13a, 14b was prepared from 13b.

Preparation of [3(Z)-benzylidene-1-carbamoylmethyl-2-methyl-3H-inden-7-yloxy]-acetic acid 14b Mp, 224–226° C. 55% yield.

$^1$H NMR ($d_6$-DMSO) δ 2.12 (3H, s), 3.64 (2H, s), 4.69 (2H, s), 6.70–6.95 (4H, m), 7.19 (1H, br.s), 7.31 (1H, s), 7.35–7.57 (5H, m), 13.2 (1H, br.s). EIMS m/z=349 (base peak, M+).

Therapeutic Use of Indene-1-Functional Compounds

The indene-1-functional compounds of the invention are believed to achieve their beneficial therapeutic action principally by direct inhibition of human sPLA$_2$, and not by acting as antagonists for arachidonic acid, nor other active agents below arachidonic acid in the arachidonic acid cascade, such as 5-lipoxygenases, cyclooxygenases, and etc.

The method of the invention for inhibiting sPLA$_2$ mediated release of fatty acids comprises contacting sPLA$_2$ with an therapeutically effective amount of compound corresponding to formulae (I), (II), (III) or a salt or a prodrug derivative thereof.

The compounds of the invention may be used in a method of treating a mammal (e.g., a human) to alleviate the pathological effects of septic shock, adult respiratory distress syndrome, pancreatitis, trauma, bronchial asthma, allergic rhinitis, and rheumatoid arthritis; wherein the method comprises administering to the mammal at least compound represented by formulae (I), (II), (III) or any combination thereof in a therapeutically effective amount. A therapeutically effective amount is an amount sufficient to inhibit sPLA$_2$ mediated release of fatty acid and to thereby inhibit or prevent the arachidonic acid cascade and its deleterious products. The therapeutic amount of compound of the invention needed to inhibit sPLA$_2$ may be readily determined by taking a sample of body fluid and assaying it for sPLA$_2$ content by conventional methods.

Pharmaceutical Formulations of the Invention

As previously noted the compounds of this invention are useful for inhibiting sPLA$_2$ mediated release of fatty acids such as arachidonic acid. By the term, "inhibiting" is meant the prevention or therapeutically significant reduction in release of sPLA$_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the indene-1-functional compounds of the invention (represented by formulae (I), (II), (III)) together with a pharmaceutically acceptable carrier or diluent therefor. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound.

The compounds of the present invention are preferably formulated prior to administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

The following pharmaceutical formulations 1 thru 8 are illustrative only and are not intended to limit the scope of the invention in any way. "Active ingredient", refers to a compound according to formulae (I), (II), (III) or a pharmaceutically acceptable salt, solvate, or prodrug derivative thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

|  |  |
| --- | --- |
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

|  |  |
| --- | --- |
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

|  |  |
| --- | --- |
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
| --- | --- |
| Isotonic saline | 1,000 ml |

The solution of the above ingredients generally is administered intravenously to a subject at a rate of 1 ml per minute.

Assay Experiments

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

Reagents:
Reaction Buffer
$CaCl_2.2H_2O$ (1.47 g/L)
KCl (7.455 g/L)
Bovine Serum Albumin (fatty acid free) (1 g/L) (Sigma A-7030, product of Sigma Chemical Co. St. Louis Mo., USA)
TRIS HCl (3.94 g/L)
pH 7.5 (adjust with NaOH)
Enzyme Buffer
0.05 $NaOAc.3H_2O$, pH 4.5
0.2 NaCl
Adjust pH to 4.5 with acetic acid
DTNB—5,5'-dithiobis-2-nitrobenzoic acid
Racemic Diheptanoyl Thio-PC
racemic 1,2-bis(heptanoylthio)-1,2-dideoxy-sn-glycero-3-phosphorylcholine
TRITON X-100™ prepare at 6.249 mg/ml in reaction buffer to equal 10 uM.
Reaction Mixture
A measured volume of racemic diheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure:

1. Add 0.2 ml reaction mixture to all wells;

2. Add 10 ul test compound (or solvent blank) to appropriate wells, mix 20 seconds;

3. Add 50 nanograms of $sPLA_2$ (10 microliters) to appropriate wells;

4. Incubate plate at 40° C. for 30 minutes;

5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ were determined by plotting log concentration versus inhibition values in the range from 10–90% inhibition.

The results of Human Secreted Phospholipase $A_2$ Inhibition tests are displayed in the Table below:

TABLE

| PLA$_2$ Chromogenic Assay Data Compound IC$_{50}$ | | |
| --- | --- | --- |
| Example No. | Scheme Comp. No. | ($\mu$M) |
| 1 Pt.N-1 | 14a | 0.91 |
| 1 Pt N-1 | 14b | 0.42 |

While the present invention has been illustrated above by certain specific embodiments, it is not intended that these specific examples should limit the scope of the invention as described in the appended claims.

We claim:

1. An indene-1-acetamide compound or a pharmaceutically acceptable salt, solvate or prodrug derivative thereof; wherein said compound is represented by the formula (I);

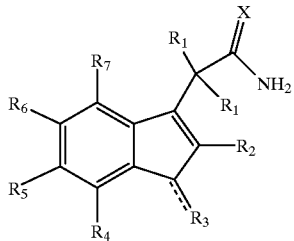 (I)

wherein;

X is oxygen or sulfur;

each $R_1$ is independently hydrogen, $C_1$–$C_3$ alkyl, or halo;

$R_3$ is selected from groups (a), (b) and (c) where;
(a) is $C_7$–$C_{20}$ alkyl, $C_7$–$C_{20}$ alkenyl, $C_7$–$C_{20}$ alkynyl, carbocyclic radical, or heterocyclic radical, or
(b) is a member of (a) substituted with one or more independently selected non-interfering substituents; or
(c) is the group —(L)—$R_{80}$; where, —(L)— is a divalent linking group of 1 to 12 atoms and where $R_{80}$ is a group selected from (a) or (b);

$R_2$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen;

$R_6$ and $R_7$ are independently selected from hydrogen, a non-interfering substituent, or the group, —($L_a$)—(acidic group); wherein —($L_a$)—, is an acid linker having an acid linker length of 1 to 10; provided, that at least one of $R_6$ and $R_7$ must be the group, —($L_a$)—(acidic group); and $R_4$ and $R_5$ are each independently selected from hydrogen, non-interfering substituent, carbocyclic radical, carbocyclic radical substituted with non-interfering substituents, heterocyclic radical, and heterocyclic radical substituted with non-interfering substituents.

2. The compound of claim 1, wherein, (A) the group $R_3$ is selected from the group consisting of

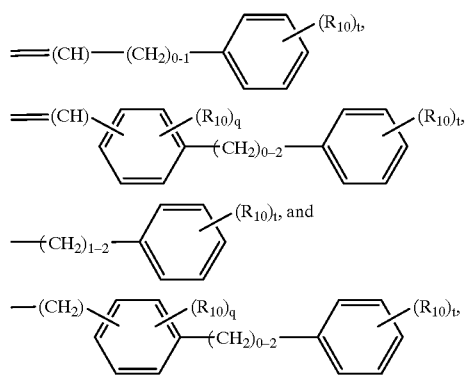

where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl, q is a number from 0 to 4, and t is a number from 0 to 5; and (B) the linking group —(L)— of $R_3$ is selected from the group consisting of:

—C≡C—,
—CH=CH—,
—CH$_2$—,
—(CH$_2$)$_2$—,
—(CH$_2$)$_s$—S—,
—(CH$_2$)$_s$—O—, and

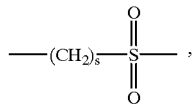

where s is 0 or 1.

(C) the (acidic group) of $R_6$ or $R_7$ is selected from:
—CO$_2$H,
—SO$_3$H,
—P(O)(OH)$_2$.

3. The compound of claim 2 wherein $R_7$ comprises an acidic group and has an acid linker with an acid linker length of 2 or 3 and the acid linker group, —($L_a$)—, for $R_7$ is represented by the formula;

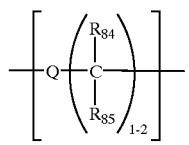

where Q is selected from the group —(CH$_2$)—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo.

4. The compound of claim 3 wherein $R_7$ comprises an acidic group and the acid linker group, —($L_a$)—, for $R_7$ is selected from the group consisting of;

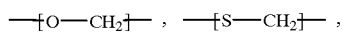

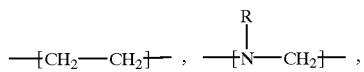

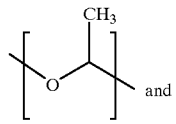

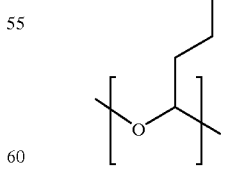

where R is H or $C_1$–$C_4$ alkyl.

5. The compound of claim 1 wherein $R_6$ comprises an acidic group and has an acid linker with an acid linker length of 3 to 10 atoms and the acid linker group, —($L_a$)—, for $R_6$ is selected from;

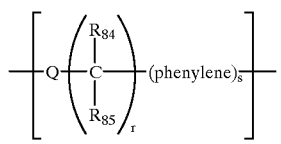

where r is a number from 1 to 7, s is 0 or 1, and Q is selected from the group —(CH$_2$)—, —O—, —NH—, and —S—, and R$_{84}$ and R$_{85}$ are each independently selected from hydrogen, C$_1$–C$_{10}$ alkyl, aryl, C$_1$–C$_{10}$ alkaryl, C$_1$–C$_{10}$ aralkyl, carboxy, carbalkoxy, and halo.

6. The compound of claim 5 wherein the acid linker, —(L$_a$)—, for R$_6$ is selected from group consisting of;

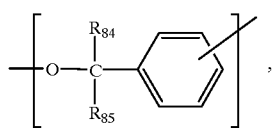

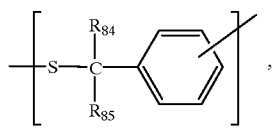

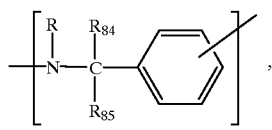

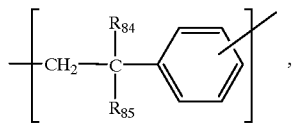

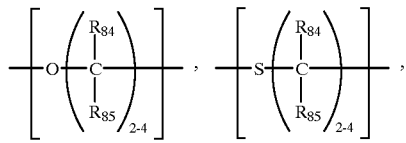

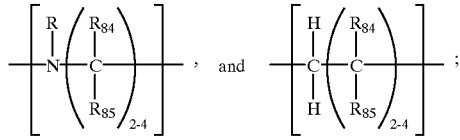

wherein; R is hydrogen or C$_1$–C$_4$ alkyl, R$_{84}$ and R$_{85}$ are each independently selected from hydrogen, C$_1$–C$_{10}$ alkyl, aryl, C$_1$–C$_{10}$ alkaryl, C$_1$–C$_{10}$ aralkyl, carboxy, carbalkoxy, and halo.

7. An indene-1-functional compound or a pharmaceutically acceptable salt, solvate or prodrug derivative thereof; wherein said compound is selected from the group represented by the formulae 14a, and 14b

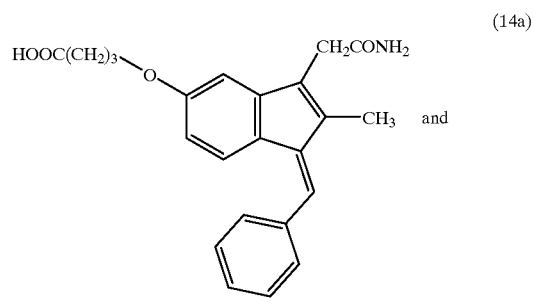

(14a)

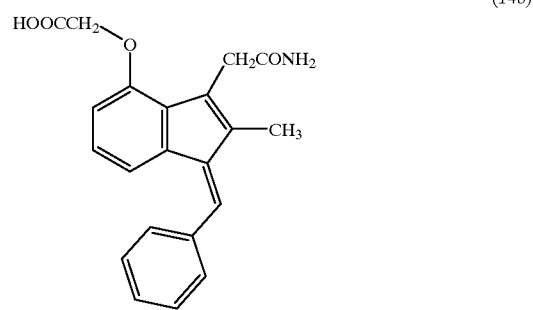

(14b)

and mixtures thereof.

8. An indene-1-acetamide compound or a pharmaceutically acceptable salt, solvate or prodrug derivative thereof; wherein said compound is represented by the formula (I);

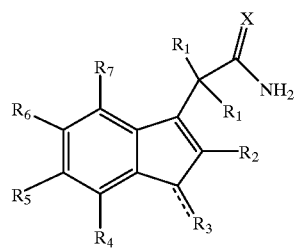

(I)

wherein;
X is oxygen;
each R$_1$ is hydrogen;
R$_2$ is selected from the group; halo, cyclopropyl, methyl, and ethyl;
R$_3$ is the group —(L)—R$_{80}$; where —(L)— is an alkylene chain of 1 or 2 carbon atoms and R$_{80}$ is selected from the group consisting of benzylidene, cycloalkyl, cycloalkenyl, phenyl, naphthyl, norbornanyl, bicycloheptadienyl, toluyl, xylenyl, indenyl, stilbenyl, terphenylyl, diphenylethylenyl, phenylcyclohexenyl, acenaphthylenyl, and anthracenyl, biphenyl, bibenzylyl and related bibenzylyl homologues represented by the formula (bb),

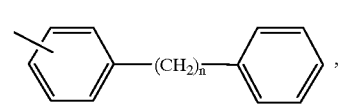

(bb)

where n is a number from 1 to 8;
R$_7$ is the group, —(L$_a$)—(acidic group); wherein the acidic group is carboxyl, and —(L$_a$)—, is an acid linker selected from the group consisting of;

$-\!\!+\!\!O\!-\!\!CH_2\!\!+\!\!-$ , $-\!\!+\!\!S\!-\!\!CH_2\!\!+\!\!-$ , $-\!\!+\!\!CH_2\!-\!\!CH_2\!\!+\!\!-$ , $-\!\!+\!\!\underset{\underset{R}{|}}{N}\!-\!\!CH_2\!\!+\!\!-$ ,

[structure: $\{-O-C(CH_3)-\}$ and ]

[structure: $\{-O-C(CH_3)(CH_2CH_2\text{-phenyl})-\}$]

where R is H or $C_1$–$C_4$ alkyl;

$R_4$, $R_5$, and $R_6$ are each independently selected from hydrogen and $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —$(CH_2)_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —$(CH_2)_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl; where n is from 1 to 8.

9. The compound [3 (Z)-benzylidene-1-carbamoylmethyl-2-methyl-3H-inden-7-yloxy]-acetic acid.

10. An indene-1-acetamide compound or a pharmaceutically acceptable salt, solvate or prodrug derivative thereof; wherein said compound is represented by the formula (I);

(I)

[structure of indene compound with substituents $R_1, R_2, R_3, R_4, R_5, R_6, R_7$, X, NH$_2$]

wherein;
X is oxygen;
each $R_1$ is hydrogen;
$R_2$ is selected from the group; halo, cyclopropyl, methyl, and ethyl;

$R_3$ is the group —(L)—$R_{80}$; where —(L)— is an alkylene chain of 1 or 2 carbon atoms and $R_{80}$ is selected from the group consisting of benzylidene, cycloalkyl, cycloalkenyl, phenyl, naphthyl, norbornanyl, bicycloheptadienyl, toluyl, xylenyl, indenyl, stilbenyl, terphenylyl, diphenylethylenyl, phenylcyclohexenyl, acenaphthylenyl, and anthracenyl, biphenyl, bibenzylyl and related bibenzylyl homologues represented by the formula (bb), (bb)

[structure: phenyl—$(CH_2)_n$—phenyl]

where n is a number from 1 to 8;

$R_6$ is the group, —$(L_a)$— (acidic group); wherein the acidic group is carboxyl, and —$(L_a)$—, is an acid linker selected from the group consisting of;

[structures showing various acid linkers with $R_{84}$, $R_{85}$ substituents including —O—C(R$_{84}$)(R$_{85}$)—phenyl—, —S—C(R$_{84}$)(R$_{85}$)—phenyl—, —N(R)—C(R$_{84}$)(R$_{85}$)—phenyl—, —CH$_2$—C(R$_{84}$)(R$_{85}$)—phenyl—, —O—(C(R$_{84}$)(R$_{85}$))$_{2-4}$—, —S—(C(R$_{84}$)(R$_{85}$))$_{2-4}$—, —N(R)—(C(R$_{84}$)(R$_{85}$))$_{2-4}$—, and —(CH(H))—(C(R$_{84}$)(R$_{85}$))$_{2-4}$—];

wherein; R is hydrogen or $C_1$–$C_4$ alkyl, $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo; and $R_4$, $R_5$, and $R_7$ are each independently selected from hydrogen and $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —(CH$_2$)$_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl; where n is from 1 to 8.

11. A pharmaceutical formulation comprising the indene-1-acetamide as claimed in claim 1 together with a pharmaceutically acceptable carrier or diluent therefor.

12. A method of treating a mammal to alleviate the pathological effects of septic shock, adult respiratory distress syndrome, pancreatitis, trauma, bronchial asthma, allergic rhinitis, and rheumatoid arthritis; wherein the method comprises administration to said mammal of at least one indene-1-acetamide as claimed in claim 1 in an amount sufficient to inhibit sPLA$_2$ mediated release of fatty acid and to thereby inhibit or prevent the arachidonic acid cascade and its deleterious products.

* * * * *